United States Patent
Raap et al.

(10) Patent No.: US 6,653,532 B1
(45) Date of Patent: Nov. 25, 2003

(54) METHODS FOR INFLUENCING THE FLOWERING BEHAVIOR OF PLANTS BY ENHANCING THE SACCHAROSE-CLEAVING ACTIVITY IN THE APICAL MERISTEM

(75) Inventors: Maik Raap, Leipzig (DE); Arnd G. Heyer, Berlin (DE)

(73) Assignee: Max-Planck-Gesellschaft zur Forderung der Wissenschafen E.V. Berlin, Munich (DE)

( * ) Notice: Subject to any disclaimer, the term of this patent is extended or adjusted under 35 U.S.C. 154(b) by 0 days.

(21) Appl. No.: 09/460,676

(22) Filed: Dec. 14, 1999

(30) Foreign Application Priority Data

Dec. 14, 1999 (DE) .......................................... 198 57 654

(51) Int. Cl.⁷ ............................ A01H 5/00; A01H 5/10; C12N 5/04; C12N 15/82
(52) U.S. Cl. ....................... 800/298; 860/290; 860/287; 435/419
(58) Field of Search ................................. 800/284, 288, 800/287, 290, 298, 323; 536/24.1; 435/410, 419, 194, 193

(56) References Cited

U.S. PATENT DOCUMENTS

| | | | |
|---|---|---|---|
| 5,866,790 A | * | 2/1999 | Hesse et al. ................. 800/205 |
| 5,981,838 A | * | 11/1999 | Jacques et al. ............. 800/284 |
| 6,025,544 A | | 2/2000 | Leggewie et al. .......... 800/290 |

FOREIGN PATENT DOCUMENTS

| | | | |
|---|---|---|---|
| DE | 198 40 028 | | 9/1998 |
| WO | 89-12386 | * | 12/1989 |
| WO | WO 95/31553 | | 5/1994 |
| WO | WO 96/21023 | | 1/1995 |
| WO | WO 97/10339 | | 9/1995 |
| WO | WO 97/27207 | | 1/1996 |
| WO | WO 96/24679 | | 2/1996 |
| WO | WO 96/11566 | | 4/1996 |
| WO | WO 96/13595 | | 5/1996 |
| WO | WO 98/16650 | | 10/1996 |
| WO | WO 98/39460 | | 9/1998 |
| WO | WO 99/24593 | | 5/1999 |

OTHER PUBLICATIONS

Chen, X. et al. "Minimal regions in the *Arabidopsis pistillata* promoter responsive to the Apetala3/Pistillata feedback control do not contain a CArG box." 2000, Sex Plant Reprod., vol. 13, pp. 85–94.*

Bradley, D, R Carpenter, L Copsey, C Vincent, S Rothestein, E Coen "Control of inflorescence architecture in Antirrhinum" Nature 379: 791–797 (Feb. 29, 1996).

Corbesier, L, P Lejeune, G Bennier "The role of carbohydrates in the induction of flowering in *Arabidopsis thaliana*: comparison between the wild type and a starchleess mutant" Planta 206: 131–137 (1998).

Bell et al., "Tobacco Plants Transformed with cdc25, a Mitotic Inducer Gene from Fission Yeast," *Plant Molecular Biology*, vol. 23, pp. 445–451, 1993.

Bernier et al., "Physiological Signals That Induce Flowering," *The Plant Cell*, vol. 5, pp. 1147–1155, Oct. 1993.

Chuck et al., "KNAT1 Induces Lobed Leaves with Ectopic Meristems When Overexpressed In Arabidopsis," *The Plant Cell*, vol. 8, pp. 1277–1289, Aug. 1996.

Dockx et al., "The Homeobox Gene ATK! *Of Arabidopsis thaliana* is Expressed in the Shoot Apex of the Seedling and in Flowers and Inflorescence Stems of Mature Plants," *Plant Molecularl Biology*, vol. 28, pp. 723–737, 1995.

Greiner et al., "Cloning of a Tobacco apoplasmic Invertase Inhibitor," *Plant Physiol*, vol. 116, pp. 733–742, 1998.

Hake et al., "Cloning Knotted, the dominant morphological mutant in maize uaing Ds2 as a Transposon Tag," *The EMBO Journal*, vol. 8, No. 1, pp. 15–22, 1989.

Hareven et al., "The Making of a Compound Leaf: Genetic Manipulation of Leaf Architecture in Tomato," *Cell*, vol. 84, pp. 735–744, Mar. 8, 1996.

Hongchang et al., "Identification of a Homeobox–Containing Gene with Enhanced Expression During Soybean (*Glycine max* L.) Somatic Embryo Development," *Plant Molecular Biology*, vol. 24, pp. 465–473, 1994.

Janssen et al., "Isolation and Characterization of Two Knotted–Like Homeobox Genes from Tomato," *Plant Molecular Biology*, vol. 36, pp. 417–425, 1998.

Kaiser et al., "Secretion–Defective Mutations in the Signal Sequence for *Saccharomyces cerevisiae* Invertase," *Molecular and Cellular Biology*, vol. 6, No. 7, pp. 2382–2391, Jul. 1986.

Kerstetter et al., "Sequence Analysis and Expression Patterns, Divide the Maize knotted1–like Homeobox Genes into Two Classes", *The Plant Cell*, vol. 6, pp. 1877–1887, Dec. 1994.

(List continued on next page.)

*Primary Examiner*—Amy J. Nelson
*Assistant Examiner*—Anne Kubelik
(74) *Attorney, Agent, or Firm*—Needle & Rosenberg

(57) ABSTRACT

The invention provides compositions and methods enabling the provision of plants showing an altered flowering behavior, and, particularly, genetically modified plants showing an early or delayed flower formation when compared to not correspondingly modified, but otherwise similar wild-type plants, as well as a tissue-specific promoter which may be utilized in a method for producing these genetically modified plants. The invention is based on the finding that the flowering behavior of plants may be influenced by enhancing the saccharose-cleaving activity specifically in the apical meristem of the plants. In this context, an enhancement of the saccharose-cleaving activity specifically in the apoplast of the apical meristem of plants results in an early flower formation whereas an enhancement of the saccharose-cleaving activity specifically in the cytoplasm of cells of the apical meristem leads to a delayed flower formation compared with corresponding not modified wild-type plants.

15 Claims, 3 Drawing Sheets

OTHER PUBLICATIONS

Krausgrill et al., "In Transformed Tobacco Cells the Apoplasmic Invertase Inhibitor Operates as a Regulatory Switch of Cell Wall Invertase," *The Plant Journal*, vol. 13, No. 2, pp. 275–280, 1998.

Lee et al., "Isolation of *Lumindependens*: a Gene Involved in the Control of Flowering Time in Arabidopsis," *The Plant Cell*, vol. 6, pp. 75–83, Jan. 1994.

Lejeune et al., "Sucrose Increase During Floral Induction in the Phloem Sap Collected at the Apical Part of the Shoot of the Long–Day Plant *Sinapis alba L.*," *Pianta*, vol. 190, pp. 71–74, 1993.

Lincoln et al., "A *knotted1–like* Homeobox Gene in Arabidopsis is Expressed in the Vegetative Meristem and Dramatically Alters Leaf Morphology When Overexpressed in Transgenic Plants," *The Plant Cell*, vol. 6, pp. 1859–1876, Dec. 1994.

Long et al., "A Member of the Knotted Class of Momeodomain Proteins Encoded by the STM Gene of Arabidopsis," *Nature*, vol. 379, pp. 66–69, Jan. 4, 1996.

Matsuoka et al., "Expression of a Rice Homeobox Gene Causes Altered Morphology of Transgenic Plants," *The Plant Cell*, vol. 5, pp. 1039–1048, Sep. 1993.

Meisel et al., "The Conserved ELK–homeodomain of Knotted–1 Contains Two Regions That Signal Nuclear Localization," *Plant Molecular Biology*, vol. 30, pp. 1–14, 1996.

Mudge et al., "T–DNA Tagging and Characterisation of a Novel Meristem–Specific Promotor from Tobacco," *Aust. J. Plant Physiol.*, vol. 25, pp. 637–643, 1998.

Ovalle et al., "Purification and Characterization of thoe Acid–Stable Proteinaceous Inhibitor of Potato Tuber Invertase by Nonideal Size Exclusion Chromatography," *J. Plant Physiol*, vol. 147, pp. 334–340, 1995.

Simon et al., "Activation of Floral Meristem Identity Genes in Arabidopsis," *Nature*, vol. 384, pp. 59–62, Nov. 1996.

Sonnewald et al., "Increased Potato Tuber Size Resulting from Apoplastic Expression of a Yeast Invertase," *Nature Biotechnology*, vol. 15, pp. 794–797, Aug. 1997.

Sonnewald et al., "Transgenic Tobacco Plants Expressing Yeast–Derived Invertase in Either the Cytosol, Vacuole or Apoplast: A Powerful Tool for Studying Sucrose Metabolism and Sink/Source Interactions," *The Plant Journal*, vol. 1, No. 1., pp. 95–106, 1991.

Vollbrecht et al., "TheDevelopmental Gene Knotted–1 is a Member of a Maize Homeobox Gene Family," *Nature*, vol. 350, Mar. 21, 1991.

Von Schaewen et al., "Expression of Yeast–Derived Invertase in the Cell Wall of Tobacco and Arabidopsis plants leads to Accumulation of Carbohydrate and Inhibition of Photosynthesis and Strongly Influences Growth and Phenotype of Transgenic Tobacco Plants," *The EMBO Journal*, vol. 9, No. 10, pp. 3033–3044, 1990.

Yokoyama et al., "The Arabidoposis ERECTA Gene is expressed in the Shoot Apical Meristem and Organ Primordia," *The Plant Journal*, vol. 15(3), pp. 301–310, 1998.

* cited by examiner

SEQUENCE LISTING

<160> NUMBER OF SEQ ID NOS: 5

<210> SEQ ID NO 1
<211> LENGTH: 1478
<212> TYPE: DNA
<213> ORGANISM: Arabidopsis thaliana
<220> FEATURE:
<221> NAME/KEY: promoter
<222> LOCATION: (1)...(1474)
<223> OTHER INFORMATION: Promoter of the KNAT1 gene (KNAT promoter)
<221> NAME/KEY: misc_feature
<222> LOCATION: (1111)...(1122)
<223> OTHER INFORMATION: Open reading frame (ORF)
<221> NAME/KEY: misc_feature
<222> LOCATION: (1269)...(1292)
<223> OTHER INFORMATION: Open reading frame (ORF)
<221> NAME/KEY: misc_feature
<222> LOCATION: (1475)...(1478)
<223> OTHER INFORMATION: Additional nucleotides added for introduction
      of a restriction endonuclease cleavage site at the 3' end

<400> SEQUENCE: 1
gtcgacctgc aggtcaacgg atctagagcc ctaggatttg acgatttata tataaataaa     60
accctaggat tttcgtttct ttttgtataa aaatgaattc ataggcactc tatacgtctc    120
atgaatcatg aaatataaat cgagattaaa tagaaaattg aatgttgacc gtggaacaga    180
acaagtgttg aaagaagtgt gtttgcagca tggtcttatc atagagccaa tagttggaaa    240
ttagcagaat atcgtataat atccactatc ctgtaaagca tttttataat tccttttttt    300
ttctcggttt ctaatgtaat cttctatccg ataacaaata ttcggatagt gtgatctctc    360
cactaatata catacgaaat tacgaaaact aaaattataa tttcatcgat ttgattaaac    420
tccaaaaaca tccaagtctt gcatcaaata tgtacatttc tatcatattg tttataattc    480
ttttttttgtt atccgtaagt tttaggcaga aacccgtaca gtgaaaccga ggaccagaac    540
aagataaacg tagtcccctc tcctaagtat agaattataa tgtgacacat gatcacaatt    600
tgttgaacga actctatgtt caaccactag actacaagaa gtatatataa atcatacata    660
ttttttttaa aacttttttc ttgactattc ttttaagaaa aaaaaaacat ttcattacta    720
gaaaatagta caaatatat cattcaacct agcaagaaac catagcctga agtagccgcg    780
aagacctagt tgcttaaaca ctgagtggtt catcttaatt cgaatattat aaaccacatt    840
ttaattaagt aaattacgta gtcttgttct aatgtataaa atagcctatg agaggaaaac    900
agaagagaga agcctttgcc ttatctcttg tcccttctct cttaccttta ttttaatttt    960
caaatatttc ttttgctcc caaagcaaac gacgtcttgt caatccactc aagccaccca   1020
acttcttcat tattgttaat ctctctctct ctctctcttt ctctcttctt ctctctttct   1080
ctttttttt tttttatttt cttctcttcc atgtcacttc cttgacgaat tctatatacc   1140
tagttcgttt tttcttcctc aaatatatct ttttcaattt atttggtttt tctttgggtg   1200
caacttcacc tcacaaaatt ttctctcttt tttatattaa tttgagttag gccttttga   1260
tttcatagat gagtcgtcta gtcgtctgga tttgatgtgg ttatagtctt acagagacct   1320
ttgattgaaa taagaacaaa agcaagaata catacatcct cttcatctta cacccatcct   1380
ttttatttt tctagggttt tatttttttt taatttattt ttttttcttt gattttata   1440
ttctctctct ctctcaaatc tttactcatc tgggatcc                           1478

<210> SEQ ID NO 2
<211> LENGTH: 1500

-continued

```
<212> TYPE: DNA
<213> ORGANISM: Arabidopsis thaliana
<220> FEATURE:
<221> NAME/KEY: promoter
<222> LOCATION: (1)...(1475)
<223> OTHER INFORMATION: Promoter of the KNAT1 gene (KNAT promoter)
<221> NAME/KEY: misc_feature
<222> LOCATION: (1111)...(1122)
<223> OTHER INFORMATION: Open reading frame (ORF)
<221> NAME/KEY: misc_feature
<222> LOCATION: (1269)...(122)
<223> OTHER INFORMATION: Open reading frame (ORF)
<221> NAME/KEY: CDS
<222> LOCATION: (1476)...(1499)
<223> OTHER INFORMATION: Coding sequence encoding N-terminal amino acid
      sequence of KNAT1

<400> SEQUENCE: 2
gtcgacctgc aggtcaacgg atctagagcc ctaggatttg acgatttata tataaataaa    60
accctaggat tttcgtttct ttttgtataa aaatgaattc ataggcactc tatacgtctc   120
atgaatcatg aaatataaat cgagattaaa tagaaaattg aatgttgacc gtggaacaga   180
acaagtgttg aaagaagtgt gtttgcagca tggtcttatc atagagccaa tagttggaaa   240
ttagcagaat atcgtataat atccactatc ctgtaaagca ttttttataat tccttttttt   300 ttctcggttt ctaatgtaat cttctatccg ataacaaata ttcggatagt gtgatctctc   360
cactaatata catacgaaat tacgaaaact aaaattataa tttcatcgat ttgattaaac   420
tccaaaaaca tccaagtctt gcatcaaata tgtacatttc tatcatattg tttataattc   480 ttttttttgtt atccgtaagt tttaggcaga aacccgtaca gtgaaaccga ggaccagaac   540
aagataaacg tagtcccctc tcctaagtat agaattataa tgtgacacat gatcacaatt   600
tgttgaacga actctatgtt caaccactag actacaagaa gtatatataa atcatacata   660 tttttttttaa aactttttttc ttgactattc ttttaagaaa aaaaaaacat ttcattacta   720
gaaaatagta caaaatatat cattcaacct agcaagaaac catagcctga agtagccgcg   780
aagacctagt tgcttaaaca ctgagtggtt catcttaatt cgaatattat aaaccacatt   840
ttaattaagt aaattacgta gtcttgttct aatgtataaa atagcctatg agaggaaaac   900
agaagagaga agcctttgcc ttatctcttg tcccttctct cttacccttta ttttaattttt   960 caaatatttc tttttgctcc caaagcaaac gacgtcttgt caatccactc aagccaccca  1020
acttcttcat tattgttaat ctctctctct ctctctcttt ctctcttctt ctctcttttct  1080 cttttttttt tttttatttt cttctcttcc atgtcacttc cttgacgaat tctatatacc  1140
tagttcgttt tttcttcctc aaatatatct ttttcaattt atttggtttt tctttgggtg  1200
caacttcacc tcacaaaatt ttctctcttt tttatattaa tttgagttag gccttttga  1260 tttcatagat gagtcgtcta gtcgtctgga tttgatgtgg ttatagtctt acagagacct  1320
ttgattgaaa taagaacaaa agcaagaata catacatcct cttcatctta cacccatcct  1380
tttttatttt tctagggttt tattttttttt taattttattt tttttttcttt gattttttata  1440 ttctctctct ctctcaaatc tttactcatc tgggt atg gaa gaa tac cag cat     1493
                                      Met Glu Glu Tyr Gln His
                                        1               5 gac aac a                                                           1500
Asp Asn <210> SEQ ID NO 3
<211> LENGTH: 8
<212> TYPE: PRT
<213> ORGANISM: Arabidopsis thaliana
```

```
<400> SEQUENCE: 3

Met Glu Glu Tyr Gln His Asp Asn
 1               5

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 4
tgtcacttct tgacgaattc                                              20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
atggatccca gatgagtaaa gatttg                                       26
```

METHODS FOR INFLUENCING THE FLOWERING BEHAVIOR OF PLANTS BY ENHANCING THE SACCHAROSE-CLEAVING ACTIVITY IN THE APICAL MERISTEM

This application claims priority to German Application No. 198 57 654.4, which was filed in Germany on Dec. 14, 1998.

BACKGROUND

1. Field of Invention

The invention concerns means and methods which enable the provision of plants showing an altered flowering behaviour and, particularly, genetically modified plants showing an early or delayed flower formation when compared to wild-type plants, i.e., not correspondingly modified, but otherwise similar plants. The invention also pertains to a tissue-specific promoter which may be utilized in a method for producing the transgenic plants according to the present invention.

2. Description of Background

In plants, the formation of flowers is a prerequisite for the sexual reproduction. Therefore, it is essential to the reproduction of plants incapable of vegetative reproduction, as well as for the formation of seeds and fruit. The time at which plants undergo the transition from merely vegetative growth to flower formation is of great importance, for example, in agriculture, horticulture and plant breeding. As well, in many cases, the number of flowers is of economic interest, e.g., in case of various useful plants (such as tomato, cucumber, zucchini, cotton, . . . ) where a higher number of flowers will possibly result in an increased yield, or in the production of ornamental plants and flowers for cutting.

In many applications, a very early flower formation of plants will be advantageous. In agriculture, for example, early flowering of various useful plants may reduce the time between sowing and harvesting and, thus, enable sowing two times a year. Alternatively, the time between flowering and harvesting may be extended and, as a result, the yields will potentially increase. As well, in plant breeding, an early flower formation may contribute to a significant shortening of the breeding process and, thus, result in an improved economic efficiency. The economic benefit of an early flowering is also evident in horticulture and in the production of ornamental plants.

The attempts made to date for elucidating the mechanisms determining the time of flower formation in plants do not allow an unambigous conclusion with respect to the decisive factors therefor. Various factors appear to be involved in a probably highly complex biological system (Bernier, 1988, Ann Rev Plant Phys Plant Mol Biol 39: 175–219). It is known for a number of plants that environmental influences determine the transition from vegetative growth to flower formation, such as light-dark cycles, temperature and water supply. Although it is known how the perception of these stimuli is effected by the plants—for this, light receptor proteins of the phytochrome system are responsible—it is unknown how the stimulus is converted or translated into physiological signals which induce the flower formation in the apical meristem. Various theories are discussed and quite a number of potential factors are taken into consideration such as flowering hormones (florigen/antiflorigen), carbohydrates, cytokinins, auxine, polyamines and calcium ions (Bernier et al., 1993, Plant Cell 5: 1147–1155).

In practice, the control of the time of flower formation by regulation of exogenous stimuli such as light-dark cycles, temperature or water supply, may be achieved only to a limited extent, for example in greenhouses. To achieve an early flower formation in plants growing under field conditions it is therefore necessary to use plants which show an early flower formation irrespective of exogenous stimuli. Plants showing early flowering may be produced by mutagenesis procedures which, however, are not applicable to all species, by plant breeding processes which, however, are very time-consuming and have to be carried out separately for every particular plant species, or by genetic engineering.

A prerequisite for the applicability of genetic engineering is that gene loci have been identified which have a significant influence on the time of flowering, and that DNA sequences are available encoding the relevant products. At present, the gene product of the CONSTANS gene from *Arabidopsis thaliana* is known. The expression of this gene causes the onset of flowering in this species. However, a selective overexpression of this gene in transgenic plants in order to influence the flowering behaviour, will not be technically feasible since a constitutive expression of the gene will lead to a severe shortening of the vegetative growth phase of the transgenic plants and, therefore, will reduce the yields. Simon et al. (1996, Nature 384: 59–62) describe an inducible system for the expression of CONSTANS which cannot be technically used since the use of steroid hormones which cause the induction, is unacceptable in agriculture.

For the species *Arabidopsis thaliana* which has been the subject of most investigations on the regulation of the time of flowering, various mutants flowering early in comparison with wild-type plants have been described (see references in Lee et al., 1994, Plant Cell 6: 75–83). However, it has not yet been possible to characterize these mutants. As well, the elucidation of the biochemical causes leading to the early flower formation has not yet been successful.

Bell et al. (1993, Plant Mol. Biol. 23: 445–451) describe tobacco plants transformed with cdc25 cDNA from *Schizosaccha-romyces pombe* which show an early flower formation and a strongly increased number of flowers due to the expression of this mitose-inducing protein. However, these plants are disadvantageous in that severe changes of the leaf morphology are observed. Particularly, the leafs of these plants are curled. Therefore, this method appears to be unsuitable for producing useful plants showing an altered flowering behaviour.

For producing intact plants showing an early flower formation, one has still to rely on classical breeding procedures or on methods utilizing mutagenesis. Any function of saccharose-cleaving proteins in the regulation of the flowering behaviour has not been considered yet.

It is true that saccharose has been repeatedly discussed as a potential component of a complex signal for the flowering induction in the apical meristem (Bernier et al., 1993, Plant Cell 5: 1147–1155; Lejeune et al., 1993, Planta 190: 71–74; Lejeune et al., 1991, Plant Physiol. Biochem. 29: 153–157); however, any influence of a saccharose-cleaving protein on the flowering behaviour is neither yet known nor to expect since according to findings of Lejeune et al. (1993, Planta 190: 71–74), in some species, an increase in the saccharose concentration at the apex is associated with the induction of flowering.

Furthermore, the expression of saccharose-cleaving proteins in transgenic plants usually has strongly detrimental effects for the growth of said plants. An expression of the enzyme invertase from *Saccharomyces cerevisiae* under the control of a constitutive promoter in tobacco plants causes necrosis in the leaves irrespective whether the protein is localized in the apoplast, cytosol or vacuole (Sonnewald et al., 1991, *Plant J*. 1: 95–106).

SUMMARY OF INVENTION

The problem underlying the present invention is to provide means and methods which make it possible to alter the flowering behaviour of plants and particularly to provide genetically modified plants which show an early or delayed flower formation compared to not-modified plants.

This problem is solved by means of the transgenic plants, promoter elements, constructs, transformed host cells, processes and uses as defined in the attached claims.

DETAILED DESCRIPTION OF INVENTION

Figure 1:
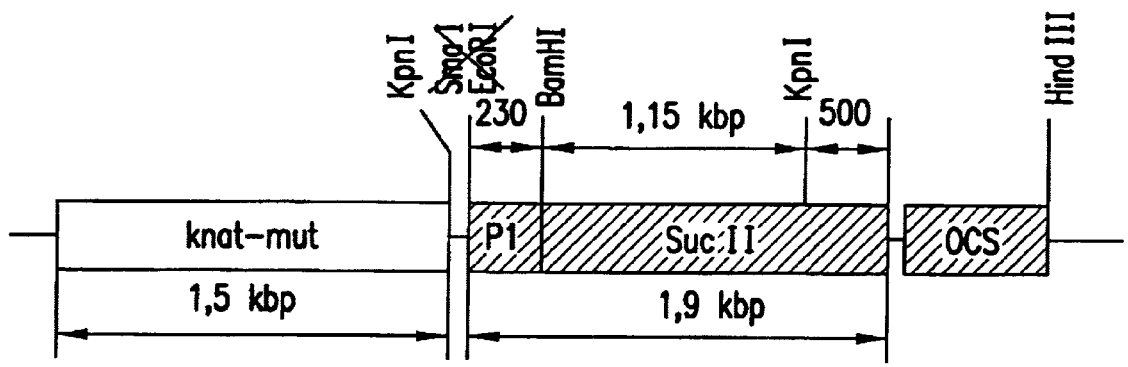
FIG. 1: Schematic depiction of the construct KNAT-AI. The yeast invertase gene (SUCII) under the control of the apical meristem specific KNAT promoter. PI-II=Part of the signal sequence of the proteinase inhibitor gene (PI-II) from potato enabling a localization in the apoplast, SUCII=yeast invertase, ocs=polyadenylation signal of the octopine synthase gene from *A. tumefaciens*.

Accordingly, under a first aspect, the present invention pertains to transgenic plants which have been genetically modified wherein the genetic modification consists in the introduction of a construct whose presence in the transgenic plants results in an enhancement of the saccharose-cleaving activity specifically in the apical meristem of said plants when compared to not-modified wild-type plants.

The genetic modification may be any genetic modification which leads to an increase of the saccharose-cleaving activity specifically in the apical meristem of plants. A corresponding genetic modification may be realized through the introduction of a construct comprising a transgene, said transgene encoding a protein having saccharose-cleaving activity and being selectively expressed in the apical meristem, thus increasing the amount of saccharose-cleaving protein present in the apical meristem. Alternatively, or in addition, the genetic modification may lead to an enhancement of the activity of saccharose-cleaving protein(s) in the apical meristem of the plants. This may be effected, for example, by the expression of an effector protein activating saccharose-cleaving protein(s) or, alternatively, inactivating an inhibitor protein deactivating saccharose-cleaving protein(s). Thus, a transgene comprised within the construct may encode an effector protein having an activating activity on saccharose-cleaving proteins. For inactivating an inhibitor protein, the construct may comprise the genetic information of a particular "antisense" nucleic acid hybridizing to mRNA or a particular "sense" nucleic acid leading to hybridization phenomena on a post-transcriptional or DNA level similar to the experiments of Faske et al., *Plant Physiol* 115, (1997), 705–715, both resulting in the elimination or at least significant reduction of the translation of an inhibitor protein of saccharose-cleaving protein(s) via homology dependent gene silencing. Examples of such an inhibitor protein are the invertase inhibitor of the apoplastic invertase from tobacco (Greiner et al., *Plant Physiol* 116, (1998), 733–742; Krausgrill et al., *Plant Journal* 13, (1998), 275–280) and the inhibitor of the invertase from potato tubers which is stable against acids (De Hostos et al., *Journal of Plant Physiol* 147, (1995), 334–340).

In the present specification, the term "construct" is meant to cover any possible form of genetic information which provides information required in the context of the present invention to a particular target cell. Accordingly, the term "construct" includes any nucleic acid molecules including any analogues thereof which comprise a sequence of bases under maintenance of the spatial structure features required for a specific recognition by the relevant cellular systems. Accordingly, the terms "construct," "nucleic acid" and "nucleic acid molecule" cover DNA, RNA, DNA-RNA-hybrids as well as synthetic analogues thereof, like PNA, so-called peptide nucleic acids wherein the sugar-phosphate-backbone of the DNA or RNA has been replaced by a peptide backbone. In PNA, the sequence of bases is bound to said peptide backbone while maintaining the conformation (spatial arrangement) of the former corresponding to that within a DNA or RNA molecule. In the present context, it is only essential that the information provided by the sequence of bases in the construct (nucleic acid molecule) will be recognized by a target cell and may be utilized for replication and/or transcription.

In a presently preferred embodiment of the invention, the genetic modification consists in introducing a construct comprising a transgene into the genome of a plant, said transgene encoding a saccharose-cleaving protein, and particularly an invertase wherein the expression of the transgene occurs specifically in the apical meristem.

In this particular context, the meaning of terms "specifically" or "specific" is that the portion of the construct responsible for the enhancement of the saccharose-cleaving activity, e.g., a transgene, "antisense" or "sense" DNA portion, particularly a transgene encoding a protein having saccharose-cleaving activity, be transcribed and, optionally, expressed in the apical meristem of a plant but not in other plant parts such as mature leaves, tubers or seeds.

Furthermore, an "apical meristem specificity" is accepted also in the case that the expression of the transgene in the apical meristem is significantly higher, for example, at least 2 to 5-fold, preferably 5 to 10-fold, particularly preferred 10 to 100-fold higher than in other parts of the plant such as mature leaves and/or tubers and/or seeds.

The meaning of the phrase "transgenic" is that a plant according to the present invention comprises at least one of the above defined constructs stably integrated in the genome, said constructs) preferably comprising a transgene encoding a protein having saccharose-cleaving activity.

In the present context, the phrase "transgene" shall mean a nucleic acid molecule that is normally not observed in a target plant or, alternatively, is normally observed in a different genetic environment within the target plant. In the latter case, a gene which is already normally present in the target plant will, additionally, be found in a genetic environment which is different from its natural or wild-type genetic environment. For example, after the introduction of the transgene into the genome of a target cell, the transgene will be found at a different genetic locus. Preferably, the transgene is integrated in a construct comprising various elements which are normally not associated with the transgene, or not in this particular order. The genetically modified plants according to the present invention may also comprise additional genetic modifications, e.g., transgenes conferring resistance against pests or plant protection agents or leading to improved yield.

The plants according to the present invention preferably comprise at least one transgene wherein the latter is particularly combined with regulatory nucleic acid sequence elements which provide for transcription of the transgene in the apical meristem of said plants, in particular with an apical meristem specific promoter and, optionally, protein targeting signal sequences which convey an apoplastic localization of the translation product of the transgene.

In a preferred embodiment of the invention, the transgene codes for a protein having saccharose-cleaving activity.

A protein having saccharose-cleaving activity which may be utilized in the present invention is characterized by being able to catalyze the cleavage of the glycosidic bond of saccharose in planta.

In a particular embodiment of the invention, the transgene codes for a saccharose synthase (E.C. 2.4.1.13.), preferably derived from plants. Nucleic acid sequences encoding saccharose synthase have been described, e.g., by Salanoubat and Belliard (Gene 60, (1987), 47–56) and are available in the EMBL database under the accession number X67125. Further saccharose synthase encoding sequences may be found in the NCBI and GenBank databases under various accession numbers such as AJ 010639 (Anabaena sp.), AJ 011319 (*L. esculentum*), AJ 012080 and AJ 001071 (both *P. sativum*), L03366 (*Oryza sativa*), AJ 001117 and AJ 000153 (both *T. aestivum*), AJ 132000 and AJ 131999 (both from *C. plantagineum*), AJ 131964 and AJ 131943 (both from *M. truncatula*).

In a further embodiment, the transgene encodes a saccharose phosphorylase (E. C. 2.4.1.7). Corresponding sequences are, i.a., described in WO 96/24679 or are available in the NCBI database under numerous accession numbers such as Z22732 (*A. vitis*), E 03420 and D 90314 (both *L. mesenteroides*), M 77351 (*S. mutans*), AF 158367 (*P. saccharophila*).

In a further embodiment, the transgene codes for a fructosyl transferase which, for example, may be of bacterial, fungal or plant origin. Sequences encoding bacterial fructosyl transferases are available in the NCBI database under various accession numbers such as X 75079 (*E. amylovora*), X 02730 (*B. subtilis*), X 52988 (*B. amyloliquefaciens*), L 34331 (*Z. mobilis*), U 91484 (*R. aquatilis*), AF 052289 (*P. syringae*) and U 34874 (*B. stearothermophilus*). Another bacterial fructosyl transferase has been described by Shiroza and Kuramitsu (*J. Bacteriol.* 170, (1988), 810–816).

Fungal fructosyl transferases may be found, e.g., under the accession number AJ 000493 (*A. foetidus*) and in the German patent application DE 19840028.4 (*A. sydowi*). Fructosyl transferases from plants are described, for example, in DE 19708774.4 (*C. scolymus*), DE 19749122.7 (*C. scolymus*) and PCT/NL96/00012 (*H. tuberosus*).

In a further embodiment of the invention, the transgene encodes a glucosyl transferase. Among the glucosyl transferases there may be cited, for example, dextran sucrases (sequences under accession numbers U38181, AF030129), amylosucrases (WO 95/31553, PCT98/05573) and alternan sucrases (DE 19905069.4).

In a preferred embodiment of the present invention, the transgene codes for an invertase (E.C. 3.2.1.26) which, for example, may be of plant, bacterial or fungal origin. Sequences encoding bacterial invertases may be found, for example, under the following NCBI database accession numbers: D 10465 and L 33403 (Z. mobilis), AF 015307 (*A. pasteurianis*), AF 084030 (*E. coli*). Fungal invertases may be found, for example, under the accession numbers V 01311, K 00540, X 07572, X 07570 (all *Saccharomyces cerevisiae*), AF 029359 and L068044 (both *A. niger*). Plant invertases may be found, for example, under the following NCBI or GenBank accession numbers: X 73601 (*A. sativa*), D10265 (*V. radiata*), AB 004558 (*L. esculentum*), AJ006067 (*A. cepa*), AF 050631, AF 03042 (*T. aestivum*), AF063246 (*P. sativum*), X 95821 (*S. tuberosum*), X 81797 and X 81796 (*B. vulgaris*), AF 155121 (*O. sativa*), Y 16262 (*D. carota*), AF 050128, AF 050129, AF 043346 and AF 043347 (all *Z. mays*), AF 030420 (*T. aestivum*).

In a particularly preferred embodiment, the transgene encodes an invertase from *Saccharomyces cerevisiae* which, in plants, is localized in the apoplast (Sonnewald et al., *Nature Biotechnology* 15, (1997), 794–797).

In a further particularly preferred embodiment, the transgene encodes an invertase from *Saccharomyces cerevisiae* which is localized in the cytosol of plant cells (Sonnewald et al., *Plant J.* 1, (1991), 95–106).

The plants according to the present invention may be distinguished from naturally occurring plants, i.a., in that they comprise at least one copy of a construct which is not naturally present in these cells or in that, if the construct comprises a transgene being already present in the genome of the target plant, said transgene has become integrated at a locus within the genome of the plant at which it is naturally not found, i.e., in a different genomic environment.

If the constructs introduced into a target cell comprise additional copies of nucleic acid molecules already present in the target cell, the inventive plants may be distinguished from the target cells before the introduction of the constructs, particularly from naturally occurring plants, particularly in that they comprise one or more additional copies of these nucleic acid molecules localized at locuses in the genome at which they are not naturally occurring. This may be determined, for example, by a Southern-blot analysis.

Furthermore, the inventive plants may be distinguished from naturally occurring plants preferably by one of the following features: if the introduced nucleic acid molecule portion of the construct which is to be transcribed, is heterologous with respect to the target plant cell/target plant, the transgenic plants harbour transcripts of the introduced nucleic acid molecules which are not naturally occuring in wild-type plants. These may be detected by Northern-blot analyses. Preferably, the plants according to the present invention comprise a protein which is encoded by a transgene comprised in the construct. This protein may be detected, e.g., by immunological methods, particularly by a Western-blot analysis. If the introduced construct comprises portions, e.g., a transgene, which are homologous to the target plant, the transgenic plants according to the present invention may be distinguished from non-transgenic plants, for example, by the additional expression of the introduced transgene. Furthermore, the transgenic plants will preferably comprise more transcripts of the relevant nucleic acid molecule. This may be detected, e.g., by Northern-blot analysis.

In the present context, the phrase "genetically modified" or "genetic modification" means that the genetic information contained in a plant is altered by the introduction of a construct and that the presence of the construct, the transcription of the construct or of parts of the construct or the expression of a transgene comprised in the construct will result in a phenotypic alteration of said plant. In this context, the phrase "phenotypic alteration" means a detectable alteration of one or more functions of a plant. For example, the plants according to the present invention show an increase of the saccharose-cleaving activity due to the presence of the construct or due to the expression of a transgene contained in the construct.

The phrase "enhancement of the saccharose-cleaving activity" or "increase of the saccharose-cleaving activity" means the enhancement or increase of the corresponding enzymatic activity in a target tissue which may be measured by established measuring methods. In the context of the present invention, the increase of the saccharose-cleaving activity may, for example, be due to one of the following phenomena:

an increase in the amount of protein having saccharose-cleaving activity and/or an increase in the activity of saccharose-cleaving protein, for example, due to the expression of an effector protein activating a saccharose-cleaving protein or inactivating an inhibitor protein deactivating a saccharose-cleaving protein.

The increase of the saccharose-cleaving activity, e.g., in plant tissue may be determined by measurement of the release of glucose or fructose from saccharose which is catalyzed by the activity of the saccharose-cleaving proteins in the tissue under investigation. Preferably, such an increase means an increase of the amount of glucose or fructose released due to catalytic, i.e., saccharose-cleaving activity of protein extracts from genetically modified plant cells, by at least 10%, preferably at least 20%, particularly at least 50% and particularly preferred at least 75% compared with the release of glucose or fructose catalyzed by protein extracts from not genetically modified plant cells.

If the enhancement of the saccharose-cleaving activity is due to an increase of the amount of one or more protein(s) having saccharose-cleaving activity, the increase of the amount of this particular protein or of these particular proteins may also be determined by Western-blot analysis. In this particular context, an "increase" means an increase of the amount of protein having saccharose-cleaving activity in relation to the total amount of protein of the plant cells when compared to corresponding not genetically modified plant cells.

It has been surprisingly found that by means of an enhancement of the saccharose-cleaving activity specifically in the apical meristem of plants the flowering behaviour of plants may be influenced.

In a particular embodiment of the present invention, for an apical meristem specific transcription, and optionally expression, of constructs which, in a cellular context, will bring about an enhancement of the saccharose-cleaving activity, the construct comprises a promoter directing the enhancement of the saccharose-cleaving activity specifically to the apical meristem. Here and in the following, the phrase "specific" shall have the same meaning as outlined above.

The promoter may be a naturally occurring promoter having the required tissue specificity, may be derived from such a promoter or may be a completely synthetical promoter designed, e.g., by use of "molecular modelling."

Promoters described as being apical meristem specific have been disclosed, for example, in WO 97/10339. Furthermore, a mutation in Brassica oleracea (cauliflower) is known which leads to an enormous development of apical meristems showing a very pronounced ramification (Sadik, 1962, *American J Bot* 49: 290–297). By use of this mutant it was possible to provide a meristem specific CDNA library and to isolate various meristem specific genes by means of substractive hybridization (Medford et al., 1991, *Plant Cell* 3: 359–370). Due to the high homology between Brassica and Arabidopsis, it was possible to identify the corresponding genes in *A. thaliana*. One clone carries the designation meri-5 (ATHMERI5G, ID: g166777, AC: M63166) and shows similarities to a xyloglucan endotransglycosylase (Medford et al., 1991). A meristem specific expression has been detected by means of a transcriptional promoter-GUS-fusion in *Arabidopsis thaliana* and tobacco (Medford et al., 1991). For the particular approach of the present invention, namely the expression of saccharose-cleaving proteins specifically in the apical meristem of plants, this promoter turned out to be not sufficiently specific when used in *Arabidopsis thaliana*.

For a 3.5 kb XbaI/BamHI promoter fragment from the ATK1 gene, a gene from *Arabidopsis thaliana* belonging to the Knotted1gene family, if used in fusion with GUS, it was possible to detect a shoot apical meristem (SAM) specific expression in transgenic Arabidopsis plants (Dockx et al., *Plant Mol. Biol.* 28, (1995), 723–737). Further meristem specific promoters have been described by Mudge et al. (*Australian Journal of Plant Physiology* 25, (1998), 637–643), Yokoyama et al. (ERECTA promoter; *Plant Journal* 15, (1998), 301–310) and Long et al. (promoter of the STM1 gene; Nature 379, (1996), 66–69).

In a preferred embodiment of the present invention, the apical meristem specific promoter is the complete KNAT promoter from *Arabidopsis thaliana* as depicted in SEQ ID NO. 1 of the attached sequence protocol. This promoter is described here for the first time and is itself a part of the present invention. But for the last four nucleotides, the sequence given in SEQ ID NO. 1 corresponds to the sequence of the promoter of the KNAT1 gene from *Arabidopsis thaliana* naturally found. The KNAT1 gene exhibits homology to the Knotted1 (KN1) gene from maize responsible for the formation of knot-shaped bulges of the leaf veins. The last four nucleotides have been added by cloning in order to introduce a restriction endonuclease recognition site suitable for the insertion of a transgene to be expressed under the control of this promoter.

The complete sequence of the 5' untranslated region of the KNAT1 gene comprising the KNAT promoter (including one more nucleotide at the 3' end) is depicted in SEQ ID NO. 2 (nt. 1 to nt. 1475). The nucleotides 1476 to 1500 represent the codons for the first N-terminal amino acids of the KNAT1 protein.

In a further preferred embodiment of the invention, the apical meristem specific promoter is a functional part of the sequence given in SEQ ID NO. 1 which directs the transcription and, optionally, expression of a coding nucleotide sequence placed under its control specifically to the apical meristem of plants. In this connection, the phrase "functional part" relates, i.a., to sequences which, despite the lack of non-essential DNA portions, still possess the desired functions such as promoter activity and tissue or organ specificity. This includes promoters comprising only one, two or more portions from the sequence depicted in SEQ ID NO. 1 wherein, for example, DNA sections within the sequence of SEQ ID NO. 1 not required for the desired functions have been deleted. An example of a corresponding promoter is a promoter having a sequence derived from SEQ ID NO. 1 wherein one or both of the open reading frames (ORF) (nt. 1111–1122; nt. 1269–1292) contained therein or one or two larger regions comprising said ORF have been deleted.

The present invention also pertains to naturally occurring variants of the promoter sequences and functional parts or fragments described herein as well as artificial or synthetic promoter sequences which may be designed, e.g., starting out from the nucleotide sequence of SEQ ID NO. 1 by chemical synthesis taking into account a particular codon usage of a plant.

Furthermore, promoters may be used which have been derived from the sequence given in SEQ ID NO. 1 or from functional parts thereof by nucleotide addition, substitution, deletion, insertion or modification provided that the required functions like promoter activity and tissue specificity with respect to the apical meristem are retained. Corresponding modifications of the sequence may aim at a further narrowing down of the promoter sequence contained therein or, e.g., at the introduction of restriction endonuclease cleavage sites suitable for cloning. For example, a promoter derived from the sequence given in SEQ ID NO. 1 or from functional parts thereof may exhibit a homology, i.e., identity, of at least 50%, preferably at least 65%, particularly at least 80%, and especially at least 90% or even at least 95% to the starting sequence.

The phrase "derived promoter" particularly includes promoters having a DNA sequence derived from the sequences depicted in the sequence protocol or parts thereof which hybridizes with the corresponding starting sequence from the sequence protocol or parts thereof under stringent conditions which will be defined below.

Functional parts of a promoter sequence include also promoter variants exhibiting an increased or reduced promoter activity compared with the wild-type promoter.

In a further embodiment of the invention, one may use a promoter of one of the KNAT1 homologous genes from the gene family of the KNOTTED1 homeobox genes provided that said promoter directs an apical meristem specific expression of a nucleotide sequence placed under its control.

Accordingly, the present invention also pertains to promoters of genes encoding a protein from the group of the KNAT1 proteins and which exhibit a homology, i.e., identity, of at least 50%, preferably at least 65%, particularly preferred at least 80% and especially preferred at least 90% to the coding region of the nucleotide sequence of the KNAT1 gene from *Arabidopsis thaliana* always provided that these promoters direct an apical meristem specific expression of a coding nucleotide sequence placed under their control.

The sequence of the KNAT1 gene from *Arabidopsis thaliana* has been described by Lincoln et al. (*Plant Cell* 6, (1994), 1859–1876) and has been deposited in the GenBank database under the accession number U14174. In the context of the present invention, KNAT1 homologous genes are preferably genes exhibiting a sequence identity of at least 50%, preferably at least 65%, particularly preferred at least 80% and especially preferred at least 90% to the coding region of the nucleotide sequence of the KNAT1 gene from *Arabidopsis thaliana*.

DNA sequences exhibiting homology to the KNAT1 gene from *Arabidopsis thaliana* may be identified, for example, by a computer-based sequence comparison with known sequences. The determination of the percentage of homology may be performed by use of commercially available computer programs such as the "Bestfit" program (Wisconsin Sequence Analysis Package, Version 8 for Unix, Genetics Computer Group, University Research Park, 575 Science Drive, Madison, Wis. 53711). The Bestfit program is based on the algorithm of Smith and Waterman (Advances in Applied Mathematics 2, (1981), 482–489) to find the segment with the highest sequence identity between two sequences. If using the Bestfit program or another sequence comparison program in order to determine whether a particular sequence is, for example, 95% identical to a reference sequence, the parameters are preferably set in such a way that the percentage of identity is calculated over the entire length of the reference sequence, allowing for homology gaps of up to 5% of the total number of nucleotides within the reference sequence. If using the Bestfit program, the so-called optional parameters are preferably left unchanged at their default values.

Alternatively, KNAT1 homologous genes may be identified by screening of cDNA or genomic libraries using the sequence deposited under the GenBank accession number U 14174 or parts thereof. Suitable screening techniques are well known to the skilled scientist (see, for example, J. Sambrook, E. F. Fritsch, T. Maniatis, (1989), "Molecular cloning: a laboratory manual," 2nd. edition, Cold Spring Harbor Laboratory, Cold Spring Harbor, N.Y.). Furthermore, a computer-based sequence comparison may also be performed on the level of the amino acid sequence using the amino acid sequence deposited under the GenBank accession number U 14174 or parts thereof.

After the identification of KNAT1 homologous cDNAs, genes or proteins, the promoters belonging to these homologous cDNAs, genes or proteins will be isolated and identified according to methods known in the art. The expression characteristics of the isolated promoters may then be analysed by experiments using a reporter gene as will be outlined below in greater detail.

The Knotted1 (KN1) gene from maize homologous to the KNAT1 gene from *Arabidopsis thaliana* was the first cloned homeobox gene from plants (Hake et al., *EMBO Journal* 8, (1989), 15–22; Vollbrecht et al., Nature 350, (1991), 241–243) and has been extensively studied. This gene was detected in the course of the investigation of dominant mutations in maize plants responsible for the formation of knot-shaped bulges of the leaf veins. This characteristic phenotype was the reason for naming the relevant gene locus KNOTTED (Gelinas et al., *American Journal of Botany* 56, (1969), 671–678; Freeling and Hake, *Genetics* 111, (1985), 617–634). After the isolation of the KN1 gene (Hake et al., *EMBO Journal* 8, (1989), 15–22), detailed investigations of the mutant showed that the phenotype is a result of the ectopic expression of the KN1 gene in the lateral vessels of the deformed leaves (Sinha and Hake, *Developmental Biology* 141, (1990), 203–210). In the wild type plant, KN1 is expressed in the shoot apical meristem (SAM) and only to a minor extent in the developing conducting vessels (Smith et al., *Development* 116, (1992), 21–30); furthermore, the gene is probably involved in the maintenance of the undifferentiated state of the meristem (Smith et al., 1992; Sinha et al., *Genes & Development* 7, (1993), 787–795; Jackson et al., *Development* 120, (1994), 405–413). The structure of the KN1 homeodomain is typical for homeoproteins and consists of an N-terminal arm and three a helices wherein the second and third helices form the typical helix-turn-helix structure (Hake et al., *Philosophical Transactions of the Royal Society of London—Series B: Biological Sciences* 350, (1995), 45–51).

In the meantime, a number of similar genes have been isolated from maize (Vollbrecht et al., *Nature* 350, (1991), 241–243; Kerstetter et al., *Plant Cell* 6, (1994), 1877–1887), tobacco (Feng and Kung, *Biochemical & Biophysical Research Communications* 198, (1994), 1012–1019), rice (Matsuoka et al., *Plant Cell* 5, (1993), 1039–1048), soybean (Ma et al., *Plant Mol. Biol.* 24, (1994), 465–473), tomato (Hareven et al., *Cell* 84, (1996), 735–744; Janssen et al., *Plant Mol. Biol.* 36, (1998), 417–425) as well as *Arabidopsis* (Lincoln et al., *Plant Cell* 6, (1994), 1859–1876). Due to the large sequence homologies in the homeodomain and in the ELK domain (ELK domain: conserved sequence of 24 amino acids situated before the homeodomain and typical for the group of homeoproteins similar to KNOTTED1 (Meisel and Lam, *Plant Mol. Biol.* 30, (1996), 1–14)), these genes are assigned to the gene family of the KNOTTED1 homeobox genes (Kerstetter et al., *Plant Cell* 6, (1994), 1877–1887). The KNAT1 gene from *Arabidopsis thaliana* appears to be very similar to the KN1 gene from maize as regards both the expression pattern and the function (Lincoln et al., *Plant Cell* 6, (1994), 1859–1876; Chuck et al., *Plant Cell* 8, (1996), 1277–1289). By means of in situ hybridization it was possible to demonstrate that, in the vegetative phase of growth, the KNAT1 RNA is particularly concentrated in the peripheral zone and the "Rib" zone of the SAM (Lincoln et al., *Plant Cell* 6, (1994), 1859–1876; Jackson et al., *Development* 120, (1994), 405–413).

The promoter activity may be measured, for example, by means of the determination of the expression rate of a particular marker gene which has been placed under the regulative control of a promoter according to the present invention. Representative examples of suitable marker genes are the beta glucuronidase (GUS) gene from *E. coli* or the green fluorescence protein (GFP) gene (Baulcombe et al., *Plant J.* 7 (16), (1993), 1045–1053). Organ or tissue specificity may be easily determined by a comparison of the expression rates of the above marker genes obtained in the various tissues or organs of a plant.

In principal, the activity of an eukaryotic RNA polymerase II promoter is determined by the synergistic cooperation of various trans-active factors (DNA binding proteins) which bind to the various cis-regulatory DNA elements present in the promoter sequence. These factors interact directly or indirectly with one or more factors of the basal transcription machinery which finally results in the formation of a pre-initiation complex near the starting point of transcription (Drapkin et al., 1993, *Current Opinion in Cell Biology* 5: 469–476). It appears to be appropriate to speak of a modular structure of eukaryotic RNA polymerase II promoters, wherein components in form of various cis elements (modules) determine the overall activity of the promoter (Tjian and Maniatis, 1994, *Cell* 77, 5–8). This modular structure has been elucidated, for example, by investigations on the cauliflower mosaic virus (CaMV) 35S promoter (Benfey and Chua, 1990, *Science* 250: 959–966; Benfey et al., 1990, *EMBO J.* 9: 1677–1684; Benfey et al., 1990, *EMBO J.* 9: 1685–1696). Due to different tissue specificities, the various restriction subfragments of the –343 to +8 (with respect to the starting point of transcription) promoter exhibit in transgenic tobacco plants, the promoter has been divided into six subdomains. The strong constitutive expression directed by the complete promoter may thus be divided into tissue specific partial activities.

Individual subdomains of the promoters according to the present invention which potentially cause tissue specificity may be identified by fusion to a cassette comprising a reporter gene placed under the control of a minimal promoter. A minimal promoter is a DNA sequence comprising a TATA box approximately 20 to 30 base pairs upstream of the starting point of transcription or an initiator sequence (Smale and Baltimore, *Cell* 57, (1989), 103–113; Zawel and Reinberg, *Proc. Natl. Acad. Sci. USA* 44, (1993), 67–108; Conaway and Conaway, *Annu. Rev. Biochem* 62, (1993), 161–190). Examples of minimal promoters are the –63 to +8 D35S promoter (Frohberg 1994, Ph.D. thesis of the FU Berlin, FB Biologie, Federal Republic of Germany), the –332 to +14 minimal patatin class I promoter and the –176 to +4 minimal PetE promoter (Pwee et al., *Plant J.* 3, (1993), 437–449).

Furthermore, relevant subdomains or cis elements of the promoter according to the present invention may also be detected by deletion analyses or mutagenesis (Kawagoe et al., 1994, *Plant J.* 5(6): 885–890). The functionality testing of such a subdomain or cis element may be carried out via the detection of a reporter gene activity in transformed cells in planta. In the context of the present invention, the phrase "a functional part of the promoter sequence" includes also such subdomains or cis elements from the nucleotide sequence given in SEQ ID NO. 1 which direct the expression of a coding nucleotide sequence placed under their control specifically to the apical meristem.

It is further known that the effectiveness of a subdomain or cis element may be significantly enhanced by multimerization. In the case of the CaMV 35S promoter, for example, a tandem dimerization of a 250 bp fragment resulted in a 10-fold increase in promoter activity (Kay et al., 1987, *Science* 230: 1299–1302). In the case of the subdomain B5 of the CaMV 35S promoter, a significant increase of the activity of the promoter construct was detected if this domain was present in form of a tetramer instead of a monomer (Benfey et al., 1990, *EMBO J.* 9: 1685–1696).

Accordingly, in a further embodiment, the invention pertains to dimers and multimers of subdomains or cis elements from the nucleotide sequence given in SEQ ID NO. 1 as well as promoters comprising said dimers or multimers.

In a further embodiment of the invention, the tissue specificity of the transcription and, optionally, of the expression is directed through the selection of an apical meristem specific enhancer which is integrated into the construct. Furthermore, by a combination of apical meristem specific enhancers with promoters which, then, may or may not be apical meristem specific, an enhancement of the promoter activity may be achieved in comparison with a wild-type promoter not comprising said enhancer(s).

Various enhancers usually causing a tissue specific enhancement of expression have been described in the literature, the tissue specificity being usually determined by the particularly utilized enhancer (Benfey et al., *Science* 250, (1990), 959–966; Benfey et al., *EMBO J.* 8, (1989), 2195–2202; Chen et al., *EMBO J.* 7, (1988), 297–302; Simpson et al., *Nature* 323, (1986), 551–554).

Furthermore, there exist enhancers such as the PetE enhancer (Sandhu et al., *Plant Mol. Biol.* 37 (1998), 885–896) which do not act in a tissue specific way and, therefore, may be utilized as merely quantitative enhancer elements in front of an apical meristem specific promoter, e.g., a promoter according to the present invention. By this, the expression of the relevant construct will be enhanced in the apical meristem without affecting the tissue specificity of the promoter.

Furthermore, synthetic enhancers may be used which may have been derived from naturally occurring enhancers and/or obtained by combination of various enhancers.

For the enhancement of the transcription, e.g., of a transgene comprised in the construct, the construct may also comprise so-called "matrix attachment regions", also called "scaffold attachment regions" (see, for example, Allen et al., *Plant Cell* 5, (1993), 603–613; WO 97/27207; WO 98/16650; Vain et al., *Plant J.* 18(3), (1999), 233–242). Through the enhancement of the transcription, an enhanced translation may be caused and thereby an enhanced amount of the gene product of a transgene, e.g., of a saccharose-cleaving protein, be produced for the target location within the plant.

After having found that the flowering behaviour of plants can be influenced by an enhancement of the saccharose-cleaving activity specifically in the apical meristem thereof, it was surprisingly noticed that a specific bringing forward or delaying of the flowering may be achieved through a compartment specific enhancement of the saccharose-cleaving activity within the apical meristem.

It has been surprisingly found that the plants according to the present invention show an early flower formation compared with corresponding not-modified wild-type plants if the saccharose-cleaving activity mediated or introduced by the construct is localized in the apoplast of the apical meristem. Conversely, a delayed flower formation compared with corresponding not-modified wild-type plants is observed if the enhancement of the saccharose-cleaving activity is localized in the cytoplasm of cells of the apical meristem.

Therefore, the invention also includes transgenic plants showing an early or delayed flower formation compared to corresponding not-modified plants.

In the context of the present invention, the phrases "not-modified plant" or "wild-type plant" relate to plants which have been used as a starting material for the production of the plants according to the present invention. Accordingly, the genetic information of not-modified or wild-type plants corresponds to that of the plants according to the present invention except for the genetic information particularly introduced for affecting the flowering behaviour.

The phrase "early flower formation" means that the transformed plants are flowering at least some days, for example, two to ten days, preferably one or more weeks, particularly two to six weeks earlier than the wild-type plants.

The phrase "delayed flower formation" means that the transformed plants are flowering at least some days, for example, two to ten days, preferably one or more weeks, particularly two to six weeks later than the wild-type plants.

In an embodiment of the present invention where the construct comprises a transgene, an apoplast specific localization of the enhanced saccharose-cleaving activity may be achieved, for example, through the provision in the construct of one or more protein targeting signal sequence(s) which direct an apoplastic localization of the protein encoded by the transgene. As a signal sequence, for example, the signal sequence of the proteinase inhibitor II gene (Keil et al., *Nucleic Acid Res.* 14, (1986), 5641–5650; von Schaewen et al., *EMBO J.* 9, (1990), 30–33) may be used or a fragment of the signal sequence of he patatin gene B33 from *Solanum tuberosum* encoding only the amino acids 1 to 33 (Rosahl et al., 1986, *Mol Gen Genet* 203: 214–220), or a fragment of the levansucrase gene from *Erwinia amylovora* (Geier and Geider, 1993, *Phys Mol Plant Pathol* 42: 387–404). Another signal sequence has been described by Oshima et al., *Nucleic Acid Research* 18, (1990), 181.

An enhancement of the saccharose-cleaving activity specifically in the cytoplasm of cells of the apical meristem may particularly be realized by use of the promoters or promoter elements described above which direct an apical meristem specific transcription and, optionally, expression of the construct causing the enhancement of the saccharose-cleaving activity in a cellular context. These promoters and promoter elements cause a transcription and, optionally, expression of the construct specifically in the cytoplasm of cells of the apical meristem.

Alternatively, the tissue specific transcription and, optionally, expression, of the construct in the cytoplasm of cells of the apical meristem may be achieved by use of an apical meristem specific enhancer sequence within the construct, as has been outlined in detail above. In the latter case, the promoter sequence may or may not be tissue specific. For this, there may be used, for example, constructs comprising an apical meristem specific enhancer in combination with a minimal promoter.

The tissue and compartment specific enhancement of the saccharose-cleaving activity in the apoplast of the apical meristem and in the cytoplasm of cells of the apical meristem, respectively, may be further enhanced by use of additional transcription enhancer elements like the above mentioned enhancers and/or "matrix attachment regions" ("scaffold attachment regions"), within the construct(s) used in the method of the present invention.

The plants according to the present invention may be of any plant species, i.e., may be monocotyledonous or dicotyledonous. Preferably, they will be agricultural useful plants, i.e., plants cultivated by man for purposes of food production or technical, particularly industrial applications. Preferably, the invention pertains to fiber producing plants (e.g., flax, hemp, cotton), oil storing plants (e.g., rape, sunflower, soybean), starch storing plants (e.g., wheat, barley, oats, rye, potato, maize, rice, pea, cassava), sugar storing plants (e.g., sugar beet, sugar-cane) and protein storing plants (e.g., legumes, cereals, soybean). The invention also relates to fruit-trees and palms.

In a further preferred embodiment, the invention pertains to forage plants (e.g., forage and pasture plants and grasses, such as alfalfa, clover, ryegrass), vegetable plants (e.g., tomato, lettuce, chicory) and ornamental plants (e.g., tulips, hyacinths). Preferred are forage plants, beans, sunflower, tomato. Particulary preferred are tobacco, maize, soybean, sugar beet, lettuce, rape and rice. Rape is especially preferred.

The present invention also concerns a process for the production of a transgenic plant showing an early flower formation compared with a wild-type plant wherein (a) a construct is introduced into a plant cell wherein the presence, complete or partial transcription or expression of said construct in a plant cell results in an enhancement of the saccharose-cleaving activity specifically in the apoplast of the apical meristem of a plant compared with a wild-type plant;

(b) a plant is regenerated from the plant cell obtained in step (a);

(c) optionally, additional plants are generated from the regenerated plant obtained in step (b).

Furthermore, the invention concerns a process for the production of a transgenic plant showing a delayed flower formation compared with a wild-type plant wherein
(a) a construct is introduced into a plant cell wherein the presence, complete or partial transcription or expression of said construct in a plant cell results in an enhancement of the saccharose-cleaving activity specifically in the cytoplasm of cells of the apical meristem of a plant, compared with a wild-type plant;
(b) a plant is regenerated from the plant cell obtained in step (a);
(c) optionally, additional plants are generated from the regenerated plant obtained in step (b).

With respect to the genetic modification to be introduced into a plant cell according to step (a) of the above processes, the same applies as has been outlined before in connection with the plants according to the present invention. The regeneration of plants according to step (b) may be performed according to methods well known to the skilled scientist. The generation of additional plants according to step (c) may be performed, e.g., by vegetative propagation (for example, by means of cuttings, tubers or via callus culture and regeneration of whole plants) or by sexual reproduction. Preferably, any sexual reproduction will be effected under controlled conditions, i.e., selected plants having particular characteristics will be crossed and propagated.

The present invention is also directed to plants obtainable by the claimed processes as well as transgenic propagation material, particularly transgenic seed, transgenic plant parts and transgenic plant cells which may be obtained from the plants according to the present invention or from the plants obtainable by the claimed processes. In the present context, the phrase "propagation material" includes any part of a plant being suitable for the vegetative or sexual propagation for the production of progenies. For a vegetative propagation, for example, cuttings, callus cultures, rhizomes or tubers will be suitable. Other propagation material includes, for example, fruit, seeds, seedlings, protoplasts, cell cultures, . . . Preferably, the propagation material will be seeds.

The invention further pertains to the use of a nucleic acid construct causing an enhancement of the saccharose-cleaving activity in a plant and comprising one or more nucleic acid portions causing a transcription and, optionally, expression of the construct or of parts thereof and/or a localization of a translation product of a transgene comprised in said construct, in the apoplast of the apical meristem or, alternatively, in the cytosol of cells of the apical meristem, for the preparation of a transgenic plant showing an early or delayed flower formation, respectively, compared to a wild-type plant. For this, the constructs described above with respect to the plants according to the present invention, are preferably used.

In a preferred embodiment, the invention is directed to the use of constructs comprising a transgene wherein the transgene will preferably encode a saccharose-cleaving protein. In a particularly preferred embodiment, the transgene will encode an invertase and the expression of said invertase will occur in particular compartments of the apical meristem; by that, transgenic plants may be prepared showing an early or delayed flower formation compared to wild-type plants.

Further objects of the invention are the above-described promoter element consisting of or comprising the DNA sequence depicted in SEQ ID NO. 1 or functional parts thereof.

As has already been outlined above, except for the last four nucleotides, the sequence of SEQ ID NO. 1 corresponds to the naturally found sequence of the promoter of the KNAT1 gene from *Arabidopsis thaliana* exhibiting homology to the Knotted1 (KN1) gene from maize responsible for the formation of knot-shaped bulges of the leaf veins. In SEQ ID NO. 1, the last four nucleotides have been added by cloning for the purpose of an introduction of a restriction endonuclease cleavage site suitable for the insertion of a genetic element or transgene to be transcribed and, optionally, expressed under the control of this promoter.

The complete sequence of the 5' untranslated region of the KNAT1 gene comprising the KNAT promoter (including one more nucleotide at the 3' end) is depicted in SEQ ID NO. 2 (nt. 1 to nt. 1475). The nucleotides 1476 to 1500 represent the codons for the first N-terminal amino acids of the KNAT1 protein.

Illustrative of a promoter element comprising a functional part of the sequence of SEQ ID NO. 1 is a promoter element having a sequence derived from SEQ ID NO. 1 wherein one or both of the short open reading frames (ORF) (nt. 1111–1122; nt. 1269–1292) contained therein or one or two larger regions comprising said ORF have been deleted. In a preferred embodiment of the invention, the latter promoters will exhibit a higher promoter activity than the promoter comprising the complete sequence of SEQ ID NO. 1.

Furthermore, the invention pertains to promoters which have been derived from the sequence given in SEQ ID NO. 1 or from functional parts thereof by nucleotide addition, substitution, deletion, insertion or modification. Particularly preferred derived promoters are characterized in that the functions of the starting sequence like promoter activity and tissue specificity with respect to the apical meristem are retained in the derivatives. Corresponding modifications of the sequence may aim, for example, at a further narrowing down of the promoter sequence contained therein, or at the introduction of restriction endonuclease cleavage sites suitable for cloning. For example, a promoter derived from the sequence given in SEQ ID NO. 1 or from functional parts thereof as a starting sequence may exhibit a homology, i.e., identity, of at least 50%, preferably at least 65%, particularly at least 80%, and especially at least 90% or even at least 95% to the respective starting sequence.

Particularly, the invention comprises promoter elements having a DNA sequence derived from the DNA sequence of SEQ ID NO. 1 or from a DNA sequence of a functional part or a combination of two or more functional parts of SEQ ID NO. 1 by nucleotide addition, substitution, deletion, insertion or modification provided that the derived promoter elements hybridize to the respective starting sequence under stringent conditions.

The invention also includes promoter variants exhibiting an increased or reduced promoter activity compared with the corresponding wild-type promoter.

In a further embodiment, the invention is also directed to promoters of the KNAT1 homologous genes from the gene family of the KNOTTED1 homeobox genes. Particularly preferred are promoters which direct an apical meristem specific expression of a nucleotide sequence placed under their control.

Accordingly, the present invention also pertains to promoters of genes encoding a protein from the group of the KNAT1 proteins and which exhibit a homology, i.e., identity, of at least 50%, preferably at least 65%, particularly preferred at least 80% and especially preferred at least 90% to the coding region of the nucleotide sequence of the KNAT1 gene from *Arabidopsis thaliana* wherein these promoters preferably direct the expression of a coding nucleotide sequence placed under their control in a plant specifically to the apical meristem of the latter. These promoters may to some extent be homologous to the promoter of the KNAT1 gene of *Arabidopsis thaliana*; thus they may exhibit, for example, a homology, i.e., identity, of at least 50%, preferably at least 65%, particularly preferred at least 80% or 85% and especially preferred at least 90% to the corresponding promoter region of the nucleotide sequence of the KNAT1 gene from *Arabidopsis thaliana*.

With respect to the promoters of the present invention and particular features thereof, reference is additionally made to the explanations given above with respect to the promoters utilizable for the production of the genetically modified plants of the present invention.

In the context of the invention, a hybridization under stringent conditions will be detectable after a hybridization procedure according to one or more of the following methods. Hybridization: up to 20 hours in PEG buffer according to Church and Gilbert (0.25 M Na$_2$HPO$_4$, 1 mM EDTA, 1% (w/v) BSA, 7% (w/v) SDS, pH 7.5 with phosphoric acid; G. M. Church, W. Gilbert, (1984), Genomic sequencing, *Proc. Natl. Acad. Sci. USA* 81: 1991–1995) at 42° C. or in standard hybridization buffers containing formamide at 42° C. or without formamide at 68° C. (J. Sambrook, E. F. Fritsch, T. Maniatis, (1989), "Molecular cloning: a laboratory manual," 2nd. edition, Cold Spring Harbor Laboratory, Cold Spring Harbor, N.Y.). Wash: 3 times for 30 min at 65° C. in 3×SSC buffer (J. Sambrook, E. F. Fritsch, T. Maniatis, (1989), "Molecular cloning: a laboratory manual," see above), 0.1% SDS.

The invention also includes constructs, particularly vectors, such as plasmids, cosmids, phagemids, bacmids, viral or phage genomes, YACs (yeast artificial chromosomes) and BACs (bacterial artificial chromosomes) comprising a promoter element according to the present invention as well as the use of the inventive promoter elements for the tissue specific expression of genes in the apical meristem of plants. The invention also pertains to any kind of host cells, particularly bacterial, fungal and transgenic plant cells as well as transgenic plants having been transformed with a construct comprising a promoter element according to the present invention.

With respect to the transgenic plants reference is additionally made to the explanations given above with respect to plants characterized in that they have been transformed with a construct leading to an enhancement of a saccharose-cleaving activity specifically in the apical meristem. A further subject-matter of the invention is a method for the production of a transgenic plant wherein the method is characterized by the following steps:

a) a construct, particularly a vector, comprising a promoter element according to the present invention is introduced into a plant cell;

b) a plant is regenerated from the plant cell obtained by step a);

c) optionally, additional plants are generated from the regenerated plant obtained by step b).

The present invention is also directed to plants obtainable by the claimed process.

Furthermore, the invention relates to propagation material, which in a preferred embodiment is transgenic, particularly seed, plant parts and/or plant cells which may be obtained from the plants according to the present invention or from the plants obtainable by the claimed processes. With respect to the phrase "propagation material" reference is made to the explanations given above.

In the following, the invention will be illustrated by means of non-limiting examples.

EXAMPLES

1. Isolation of the KNAT1-promoter From *Arabidopsis thaliana*

The Knotted1 (KN1) gene from maize has been isolated in 1989 (Hake et al., 1989). This gene has been detected in the course of investigations on dominant mutations in maize plants leading, i.a., to the formation of knot-shaped bulges of the leaf veins.

The cDNA sequence of the homologous gene from *Arabidopsis thaliana* is known and has been deposited in the GenBank database under the accession number U14174. The sequence comprises 384 bp 5' from the ATG start codon (Lincoln et al., 1994, *Plant Cell* 6: 1859–1876); however, the promoter of the KNAT1 gene is not yet known.

For the isolation of the KNAT1 promoter, an *Arabidopsis thaliana* genomic library was screened with a DNA fragment of 370 base pairs (bp). This fragment had been amplified from genomic DNA of *Arabidopsis thaliana* by use of the PCR technique utilizing the primers KNAT-for and KNAT-mut, the sequence of which being presented below. The sequence comprises the known 5' portion upstream of the ATG start codon. The primer KNAT-mut comprised a sequence alteration resulting in a mutation of the ATG start codon to produce a recognition sequence for the restriction endonuclease BamHI. The sequence of the primers is given below:

KNAT-for 5' TGT CAC TTC TTG ACG AAT TC (SEQ ID NO:4) KNAT-mut 5' ATG GAT CCC AGA TGA GTA AAG ATT TG (SEQ ID NO:5)

The amplified fragment was blunt end ligated into the EcoRV cleaved vector pKS and was used for screening of a genomic λ-phage library.

The SalI/XbaI digestion of the DNA of a phage clone detected by hybridization to the above fragment produced a fragment of 2.1 kbp which hybridized in a Southern experiment with the PCR probe. This fragment was ligated into the pKS vector which had been opened with SalI/XbaI. The clone was designated pKNAT-KS-nonmut and the promoter region was completely sequenced. The promoter sequence is depicted in SEQ ID NO. 1.

The promoter part 3' from the StuI cleavage site was removed by StuI/XbaI restriction and a fill-in reaction of the XbaI cleavage was performed by means of the T4 polymerase. Then it was possible to blunt end ligate the 225 bp StuI/EcoRI (+T4 polymerase reaction) fragment from pKNAT5 into the vector. The construct was named pKNAT-mut and comprises about 1.5 kbp of promoter sequence including the 5'-NTR up to the mutated ATG.

2. Investigations on the Specificity of the KNAT1 Promoter

Since the expression characteristics of the KNAT1 promoter have not yet been investigated in transgenic plants the functionality thereof was first tested in form of a transcriptional fusion with the GUS reporter gene in transgenic Arabidopsis plants. For this, the 1.5 kbp SalI/XbaI promoter fragment was cloned into the identically cleaved vector pGPTV-HPT (Becker et al., 1992, *Plant Mol Biol* 20:

1195–1197) in front of the UIDA-gene. The construct was named pKNAT-GUS and was transferred into the *A. tumefaciens* strain GV2260 for the subsequent transformation of *A. thaliana*. The transformation of *Arabidopsis thaliana* plants was performed according to known methods (Schmidt and Willmitzer, 1989, *Mol Gen Genet* 220: 17–24). A result of the analysis of transgenic plants was the detection of a KNAT1 promoter driven specific expression of the UIDA gene in the apical meristem of transgenic *Arabidopsis thaliana* plants during the vegetative growth phase. After the development of the inflorescence, an expression of the UIDA gene could also be detected in the stem of the inflorescence.

3. Synthesis of the Constructs KNAT-AI and KNAT-CI

The coding region of the SUC2 gene from *Saccharomyces cerevisiae* which had already been used for the expression of yeast invertase in tobacco plants (Sonnewald et al., 1991, *Plant J* 1: 95–106) was cloned as transcriptional fusion to the KNAT1 promoter for an apical meristem specific expression. For this, the vector KNAT-Bin was constructed. The vector comprised the promoter fragment of the KNAT1 gene from *Arabidopsis thaliana* of approximately 1.5 kb as a SalI (filled-in)/XbaI (filled-in) fragment in the vector pBinAR-Hyg (Abel, 1995, "Untersuchungen zur Funktion von Stärke-Synthasen in der Kartoffel (Solanum tuberosum L.)." Ph.D. thesis., FU Berlin, Berlin, Federal Republic of Germany) which had been opened by digestion with the restriction endonucleases EcoRI (filled-in) and Asp718 (filled-in) thereby removing the CaMV 35S promoter which had originally been inserted in pBinAR-Hyg.

For the localization of the yeast invertase in the apoplast the entire PI-II/SUCII fusion including the OCS polyadenylation sequence (von Schaewen et al., 1990, *EMBO J* 9: 3033–3044)) was transferred into the vector KNAT-Bin. The resulting vector was named KNAT-AI (FIG. 1).

Figure 2:
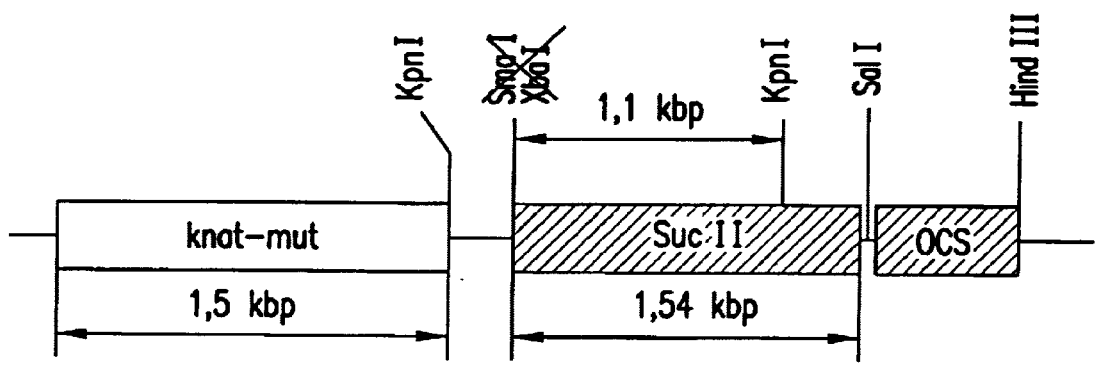
FIG. 2: Schematic depiction of the construct KNAT-CI. The yeast invertase gene (SUCII) under the control of the apical meristem specific KNAT promoter. SUCII=yeast invertase, ocs=polyadenylation signal of the octopine synthase gene from *A. tumefaciens*.

A truncated SUCII gene was used for the cytoplasmatic localization and comprised the region from nucleotide (nt.) 785 (ATG) to nt. 2383 (TAA) of the published nucleotide sequence (Accession No.: M13627, Kaiser and Botstein, 1986, *Mol Cell Biol* 6: 2382–2391). This fragment could be ligated as a XbaI (filled-in)/SalI fragment into the SmaI/SalI opened KNAT-Bin vector (FIG. 2). The construct was named KNAT-CI and, like the KNAT-AI-Vektor, was transferred into the *A. tumefa-ciens-Stamm* GV 2260 for the subsequent transformation of *A. thaliana*.

4. Analysis of Transgenic Plants Invertase Activity

Seeds from Arabidopsis plants transformed with the constructs KNAT-AI and KNAT-CI, respectively, were sown on hygromycin containing media and subsequently transferred into soil. The expression characteristics of the transgene were determined for the plants of the various lines via the determination of the invertase activity. For determining the invertase activity, the inflorescence bud was used since the analysis of the promoter specificity in the KNAT-GUS plants revealed an enhanced GUS expression in this region (see Example 2). This is advantageous in that it is still possible to harvest seeds for subsequent flowering experiments since, after the removal, the inflorescence bud will form anew.

Both for the KNAT-AI and the KNAT-CI transformation, independent lines showing an increased invertase activity could be detected. In the KNAT-AI lines, the invertase activity was increased up to 3-fold compared with the wild type (see FIG. 3c) and in the KNAT-CI lines up to 2-fold (see FIG. 4c).

Flowering Behaviour

Seeds from selected lines showing an increased invertase activity were used for two separate flowering experiments.

(a) Experiment I

The seeds were sown into soil and, for germination, the seeds were vernalized for four nights (4° C.). After additional 6 days surplus plants were removed so that one plant per pot remained. The number of rosette leaves which, in the case of *Arabidopsis thaliana*, is preferably used for the determination of the age of a plant, was counted for the determination of the time of flowering when cultivated under short day (KT: phytotron; amount of light: 145–150 $\mu$mol/m$^2$/s; 8 h light, 16 h dark) and long day (LT: phytotron; amount of light: 145–150 $\mu$mol/m$^2$/s; 16 h light, 8 h dark) conditions.

Figure 3:
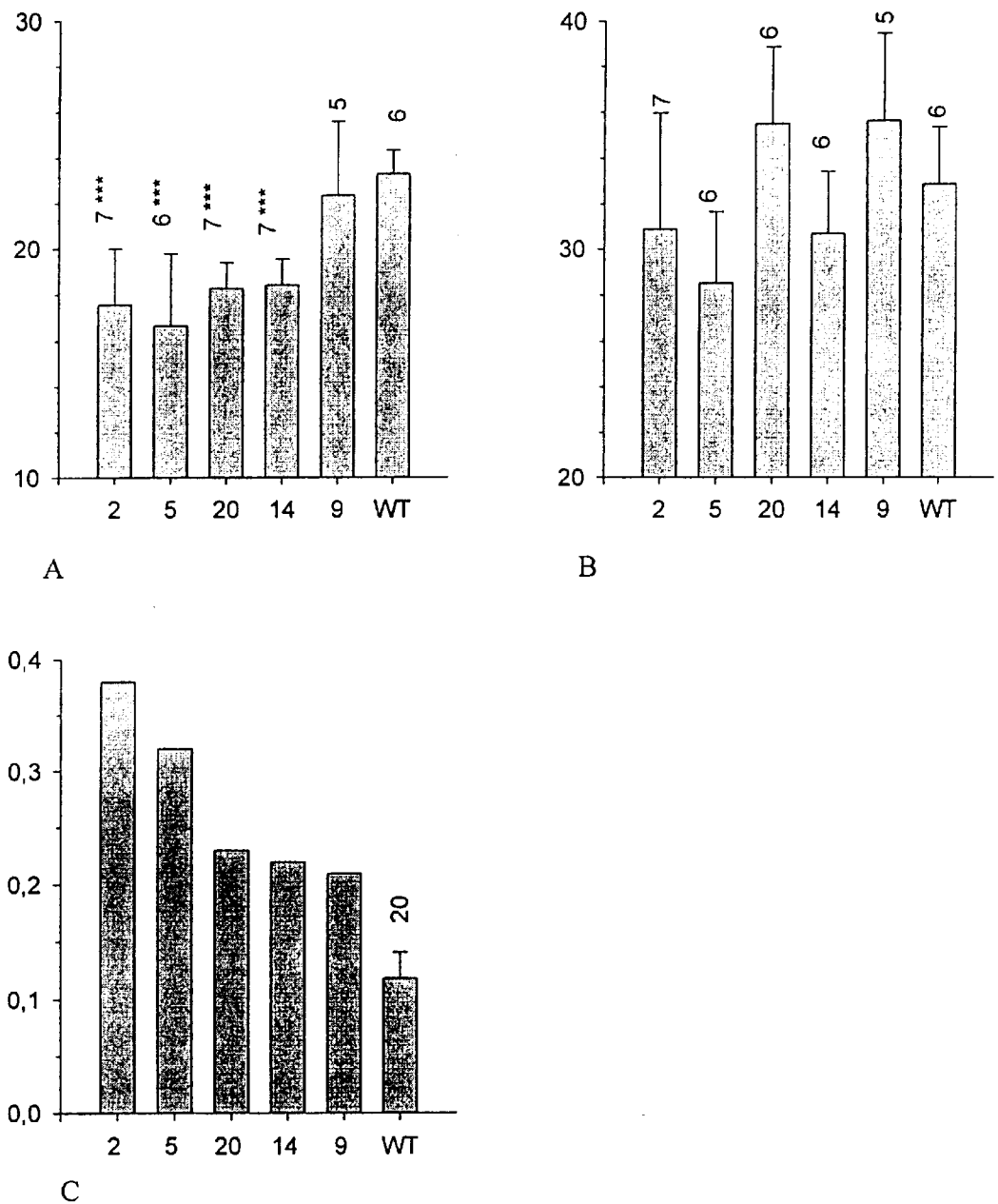
FIG. 3: Influence of the apical meristem specific expression of yeast invertase with apoplastic localization on the flowering behaviour of transgenic Arabidopsis lines. The flowering behaviour of the KNAT-AI lines was investigated in the T2 generation under long day (A) and short day (B) conditions. For the determination of the invertase activity (C) the inflorescence of the T1 generation was used (bars represent the standard deviations; numbers=number of individuals; significance according to Students t-test: p<0,01 =***). Y-axes in A and B: number of rosette leaves. Y-axis in C: invertase activity in mmol hexose/min * g fresh weight. X-axes in A–C: No. of transgenic line; WT=wild type.

The transgenic invertase lines were flowering like the wild type under KT conditions (see FIG. 3b). Differences in the number of rosette leaves appeared not to be significantly different from the wild type.

Under inductive LT conditions, however, an altered flowering behaviour could be observed in the KNAT-AI lines (see FIG. 3a). The plants from 4 of the 5 investigated transgenic lines having the invertase localized in the apoplast were already flowering when having 10 rosette leaves less than the wild type. The plants of line 9 showing an only slightly enhanced invertase activity in the T1 generation (see FIG. 3c) were flowering like the wild type.

Figure 4:
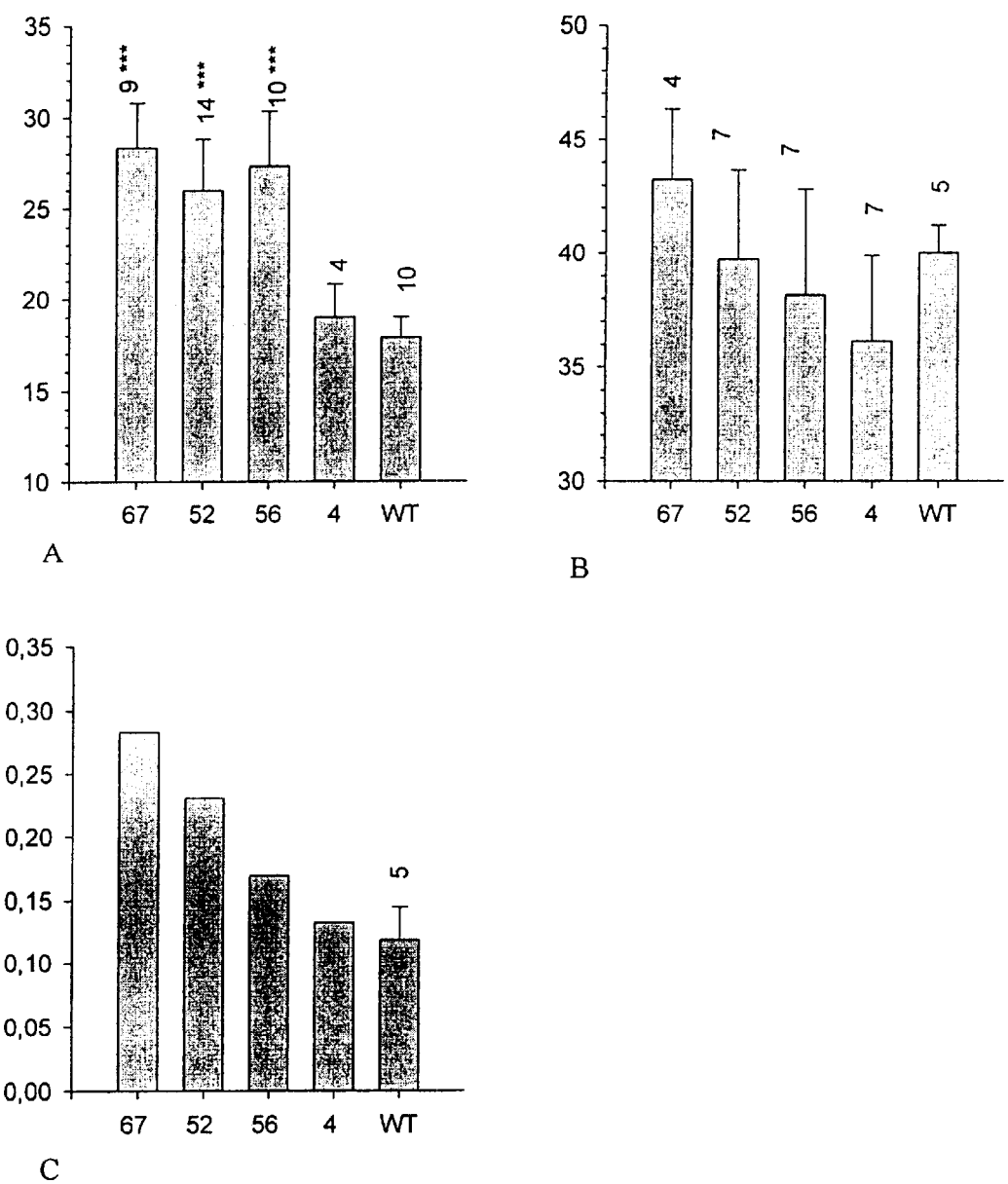
FIG. 4: Influence of the apical meristem specific expression of yeast invertase with cytoplasmatic localization on the flowering behaviour of transgenic Arabidopsis lines. The flowering behaviour of the KNAT-CI lines was investigated in the T2 generation under long day (A) and short day (B) conditions. For the determination of the invertase activity (C) the inflorescence of the T1 generation was used (bars represent the standard deviations; numbers=number of individuals; significance according to Students t-test: p<0,01 =***) Y-axes in A and B: number of rosette leaves. Y-axis in C: invertase activity in mmol hexose/min * g fresh weight. X-axes in A–C: No. of transgenic line; WT=wild type.

While the KNAT-AI lines exhibited an early flowering phenotype under LT conditions, under the same conditions, the KNAT-CI-lines were flowering significantly later than the wild type (see FIG. 4a). Thus, the average number of rosette leaves formed until flowering was increased by 7 to 10 in 3 of the 4 investigated KNAT-CI lines compared with the wild type. Only the plants of line 4 were flowering unchanged; these plants, however, showed only a slightly enhanced invertase activity in the starting generation (see FIG. 4c).

(b) Experiment II

The seeds were pregerminated on soil for two weeks under short day conditions (8 h light/16 h dark; temperatures: 18° C. (day), 6° C. (night)). Transplanted germinated seeds (size of cotyledon: approx. 2 mm) were planted in soil consisting of a 1:1 mixture of GS90 substrate and vermiculite. Then, the plants were cultivated in a greenhouse under the following conditions:

relative humidity: 60 to 70%, day time temperature: 20 to 22° C., night temperature: 18 to 20° C., amount of light: 280 to 300 $\mu$mol/m$^2$/s light/dark cycle: 16 h/8 h.

Under greenhouse conditions, an altered flowering behaviour could be detected both in the KNAT-AI lines (plants flowering approximately two days earlier than the wild type) and in the KNAT-CI lines (plants flowering approximately 3 to 5 days later than the wild type).

What is claimed is:

1. A transgenic plant, wherein the transgenic plant has been transformed with a construct comprising the KNAT-1 promoter of SEQ ID NO:1 and operably linked to a transgene that encodes a protein with saccharose-cleaving activity, wherein the construct leads to an enhancement of the saccharose-cleaving activity specifically in the apical meristem of the transgenic plant, and also leads to altered timing of flowering compared to a wild-type plant.

2. The transgenic plant of claim 1, wherein the transgene encodes a protein selected from the group consisting of invertases, saccharose phosphorylases, saccharose synthases, fructosyl transferases and glucosyl transferases.

3. The transgenic plant of claim 2, wherein the transgene encodes an invertase from *Saccharomyces cerevisiae*.

4. A transgenic plant, wherein the transgenic plant has been transformed with a construct comprising the apical meristem specific KNAT promoter having the sequence disclosed in SEQ ID NO:1 or having a sequence produced from SEQ ID NO:1 wherein one or both regions consisting of nucleotide residues 1111–1122 and 1269–1292 have been deleted, operably linked to a transgene that encodes a protein with saccharose-cleaving activity, wherein the construct leads to an enhancement of the saccharose-cleaving activity specifically in the apical meristem of the transgenic plant, and also leads to altered timing of flowering compared to a wild-type plant.

5. The transgenic plant of claim 1, wherein the construct comprises an enhancer sequence functionally linked to the KNAT-1 promoter SEQ ID NO: 1.

6. The transgenic plant of claim 1, wherein the saccharose-cleaving activity in the apoplast of the apical meristem is enhanced relative to a wild-type plant.

7. The transgenic plant of claim 6, wherein the construct comprises a nucleic acid encoding a apoplastic targeting signal sequence operably transgene.

8. The transgenic plant of claim 7, wherein the apoplastic targeting signal sequence is selected from the group consisting of pin 2 from *Solanum tuberosum*, the signal sequence of the patatin gene B33 from *Solanum tuberosum* and the signal sequence of the levan sucrase from *Erwinia amylovora*.

9. The transgenic plant of claim 1, wherein the transgenic plant is a fiber producing, oil storing, starch storing, sugar storing or protein storing plant.

10. The transgenic plant of claim 1, wherein the transgenic plant is a forage, vegetable or ornamental plant.

11. A method for production of a transgenic plant with early flower formation compared with a wild-type plant, wherein the method comprises the following steps:

(a) introducing into a plant cell a construct comprising the KNAT-1 promoter of SEQ ID NO:1 operably linked to a transgene, wherein the transgene encodes a protein having saccharose cleaving activity;

(b) regenerating a transgenic plant from the plant cell obtained from step (a), thereby producing a transgenic plant that has enhanced saccharose cleaving activity in the apoplast of the apical meristem of the plant and has early flower formation compared to a wild-type plant.

12. A method for production of a transgenic plant with delayed flower formation compared with a wild-type plant, wherein the method comprises the following steps:

(a) introducing into a plant cell a construct comprising the KNAT-1 promoter of SEQ ID NO:1 operably linked to a transgene, wherein the transgene encodes a protein having saccharose cleaving activity;

(b) regenerating a transgenic plant from the plant cell obtained from step (a), thereby producing a transgenic plant that has enhanced saccharose cleaving activity in the cytoplasm of the apical meristem of the plant and has early flower formation compared to a wild-type plant.

13. A transgenic plant obtained by a method of claim 11.

14. Transgenic material obtained from the transgenic plant of claim 1, wherein the material is selected from the group consisting of transgenic propagation material, transgenic seeds, transgenic plant parts and transgenic plant cells.

15. The method of claim 12, wherein the transgene encodes an invertase.

* * * * *

UNITED STATES PATENT AND TRADEMARK OFFICE
CERTIFICATE OF CORRECTION

PATENT NO. : 6,653,532 B1
DATED : November 25, 2003
INVENTOR(S) : RAAP et al.

It is certified that error appears in the above-identified patent and that said Letters Patent is hereby corrected as shown below:

<u>Title page,</u>
Item [30], Foreign Application Priority Data, change "December 14, 1999" to read -- December 14, 1998 --.

Signed and Sealed this

Fourth Day of May, 2004

JON W. DUDAS
*Acting Director of the United States Patent and Trademark Office*